United States Patent [19]

Evers

[11] Patent Number: Plant 7,660

[45] Date of Patent: Oct. 1, 1991

[54] ROSE PLANT OSIANA

[75] Inventor: Hans Evers, Uetersen, Fed. Rep. of Germany

[73] Assignee: Bear Creek Gardens, Inc., Medford, Oreg.

[21] Appl. No.: 531,800

[22] Filed: May 31, 1990

[51] Int. Cl.[5] ..... A01H 5/00

[52] U.S. Cl. ..... Plt./18

[58] Field of Search ..... Plt./11, 14, 15, 16, Plt./17, 18

*Primary Examiner*—James R. Feyrer

*Attorney, Agent, or Firm*—Klarquist, Sparkman, Campbell, Leigh & Whinston

[57] ABSTRACT

A hybrid tea class rose having blooms of pastel-cream, slightly darker in the center, large, pointed buds and high centered flowers, medium dark green and large, long leaves, and strong, long stems (80 to 100 cm) with very few thorns.

1 Drawing Sheet

This present invention relates to a new and distinct variety of rose plant of the hybrid tea class which was originated by me by crossing two unnamed seedlings.

The primary objective of this breeding was to produce a new rose variety having outstanding, long lasting blooms of a unique orange-white (pastel-cream) color. The objective was substantially achieved along with other desirable improvements as evidenced by the following unique combination of characteristics which are outstanding in the new variety and which distinguish it from its parents, as well as from all other varieties of which I am aware:

1. Blooms of pastel-cream, slightly darker in the center.
2. Large, pointed bud and high centered flower.
3. Medium dark green and large, long leaves.
4. Strong, long stems (80 to 100 cm) with very few thorns.

Asexual reproduction of this new variety by budding, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart, except where ordinary dictionary significance of color is indicated.

Parentage:

*Seed parent.*—An unnamed seedling.

*Pollen parent.*—An unnamed seedling.

Classification:

*Botanical.*—*Rosa hybrida.*

*Commercial.*—Hybrid tea.

FLOWER

Observations made from specimens grown in a greenhouse environment in Somis, Calif., from June to October, 1989.

Blooming habit: Continuous.

Bud:

*Size.*—2 to 2¼ inches when the petals start to unfurl.

*Form.*—Long, pointed ovoid.

*Color.*—When sepals first divide: Orange-white Group 159A to B. When half blown, the upper sides of the petals are: Outer petals are Orange-White Group 159A to B with the inner petals colored Orange Group 27A; and the lower sides of the petals are: Same color.

*Sepals.*—Color: Green Group 138B.

*Surface texture: Covered in fine hairs. There are three normally appendaged sepals. There are two unappendaged sepals with hairy edges.*

*Receptacle.*—Color: Medium green. Shape: Funnel. Size: Medium to large (½ inch wide×½ inch long). Surface: Smooth.

*Peduncle.*—Length: Medium, 3 inches long. Surface: Rough, with small prickles. Color: Medium green. Strength: Stiff, erect, heavy.

Bloom:

*Size.*—Very large. Average open size is 5 to 6 inches across.

*Borne.*—Singly.

*Stems.*—Very long, strong. Stems average more than 26 inches in length and are very strong.

*Form.*—When first open: High centered. Permanence: Retains its form to the end, outer petals curl back, quill fashion.

*Petalage.*—Number of petals under normal condition: 30 to 35.

*Color.*—The upper side of the petals is: Orange-white Group 159A to B, deepening to Orange Group 27A on the inner petals. The reverse side of the petals is: Same. The base of petals is: Small yellowish half moon at the point of attachment. The major color on the upper side is: Orange-white Group 150A to B, deepening to Orange Group 27A.

*Variegations.*—None.

*Discoloration.*—The general tonality at the end of the first day: None. At the end of the third day: Color intensifying by becoming light orange in the center of the flower.

*Fragrance.*—Moderate.

Petals:

*Texture.13* Thick.

*Shape.*—Round.

*Form.*—Tips slightly recurved, edges slightly quilled.

*Arrangement.*—Imbricated. Petaloids in the center: None.

*Persistence.*—Drop off cleanly.

*Lastingness.*—On the plant: Long, 7 days. As a cut flower: Long, 7 to 10 days.

Reproductive parts:

*Anthers.*—Size: Large. Quantity: Many. Color: Yellow. Arrangement: Regular around styles.

*Filaments.*—Color: Yellow.

*Pollen.*—Color: Gold yellow.

*Styles.*—Color: Very light pink.

*Stigmas.*—Color: Yellow.

Form: Bush.

Growth: Very vigorous, upright, branching.

Foliage: Number of leaflets on normal mid-stem leaves: 5, or occassionally 7.

*Size.*—Very large to large, 7 inches.

*Quantity.*—Normal.

*Color.*—New foliage: Reddish. Old foliage: Dark green.

Leaflets:

*Shape.*—Broadly oval to oval.

*Texture.*—Upper side: Leathery.

*Edge.*—Serrated.

*Serration.*—Single, small.

*Petiole rachis.*—Color: Reddish.

*Petiole underside.*—Smooth, with occasional prickles.

*Stipules.*—Medium, bearded ($\frac{1}{2}$ to $\frac{3}{4}$ inches).

*Disease resistance.*—Resistant to powdery mildew under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Few. On laterals from main canes: Ordinary.

*Form.*—Medium, hooked downward, $\frac{1}{4}$ inch long.

*Color when young.*—Red.

*Position.*—None.

Small prickles:

*Quantity.*—On main stalks: None. On laterals: None.

*Color.*—Green.

I claim:

1. A new and distinct variety of rose plant of the hybrid tea class, substantialy as herein shown and described, characterized particularly as to novelty by the unique combination of its pastel-cream, long lasting, high centered blooms on long (80 to 100 cm), strong stems having very few thorns, and its medium dark green, large, long leaves.

* * * * *

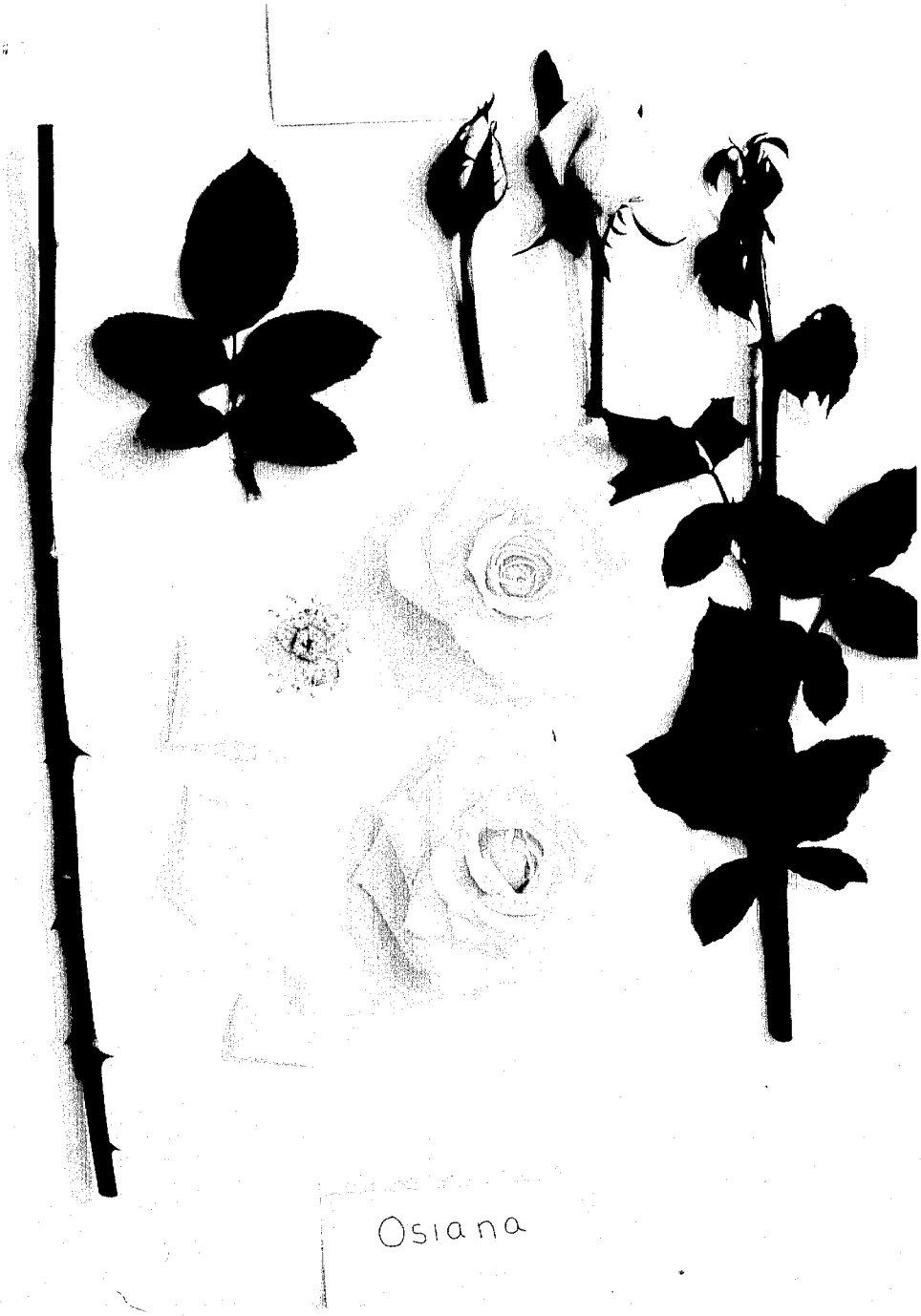
Osiana